United States Patent
Korkin et al.

(10) Patent No.: US 9,448,189 B2
(45) Date of Patent: Sep. 20, 2016

(54) APPARATUS AND METHOD FOR FLUID PHASE FRACTION DETERMINATION USING X-RAYS

(71) Applicant: Schlumberger Technology Corporation, Sugar Land, TX (US)

(72) Inventors: Roman Vladimirovich Korkin, Berdsk (RU); Lev Zakharov, Bergen (NO); Oleg Zhdaneev, Amiens (FR); Joel Lee Groves, Leonia, NJ (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 96 days.

(21) Appl. No.: 14/345,398

(22) PCT Filed: Sep. 28, 2012

(86) PCT No.: PCT/IB2012/055179
§ 371 (c)(1),
(2) Date: Mar. 17, 2014

(87) PCT Pub. No.: WO2013/046159
PCT Pub. Date: Apr. 4, 2013

(65) Prior Publication Data
US 2014/0355737 A1 Dec. 4, 2014

(30) Foreign Application Priority Data
Sep. 29, 2011 (EP) .................................. 11183252

(51) Int. Cl.
*G01N 23/12* (2006.01)
*G01N 23/083* (2006.01)
(Continued)

(52) U.S. Cl.
CPC .................. *G01N 23/12* (2013.01); *G01F 1/34* (2013.01); *G01N 23/083* (2013.01);
(Continued)

(58) Field of Classification Search
CPC ... G01N 23/083; G01N 23/087; G01N 23/12
USPC .................................................. 378/53, 98.9
See application file for complete search history.

(56) References Cited

U.S. PATENT DOCUMENTS 5,479,020 A * 12/1995 Mohn ..................... G01N 23/12
250/356.1
5,689,540 A * 11/1997 Stephenson ............ G01N 23/22
378/51
(Continued)

FOREIGN PATENT DOCUMENTS

| EP | 2275804 | 1/2011 |
|---|---|---|
| WO | 99/10712 | 3/1999 |
| WO | 2008/032265 | 3/2008 |

Primary Examiner — Allen C. Ho
(74) Attorney, Agent, or Firm — Cameron R. Sneddon

(57) ABSTRACT

An apparatus for determining fluid phase fraction of a multiphase fluid mixture (13) comprises: —a x-ray generator (20) arranged to emit a x-ray radiation spectrum comprising a low energy region and a high energy region, the high energy region including a Bremsstrahlung spectrum; —a pipe section (27) through which the multiphase fluid mixture (13) flows comprising a measurement section (28), said measurement section (28) being coupled to said x-ray generator (20); —a detector (30) coupled to said measurement section (28) and arranged to detect x-ray radiation that has passed through said multiphase fluid mixture (13), the detector (30) being coupled to a multichannel analyzer (32) producing a measurement output comprising a low energy (LE) and high energy (HE) measurement counts; wherein the measurement output further comprises a low energy (LV) and high energy (HV) control counts, in a low energy and high energy control windows located on an edge of the Bremsstrahlung spectrum, respectively; and wherein the apparatus further comprises an electrical parameter control arrangement (33) coupled to the x-ray generator (20) and the detector (30), the electrical parameter control arrangement (33) being arranged to calculate a first ratio of the high energy control count relative to the low energy control count ($R_V$=HV/LV) and a second ratio of the high energy measurement count relative to the low energy measurement count ($R_E$=HE/LE), and to adjust the electrical operation of the x-ray generator (20) based on an electrical parameter control function ($F_C(V)$) of said ratios that minimize a dependence of the electrical operation of the x-ray generator on the fluid phase fraction of the multiphase fluid mixture (13) flowing in the measurement section (28).

16 Claims, 6 Drawing Sheets

(51) Int. Cl.
*G01N 23/087* (2006.01)
*G01N 33/28* (2006.01)
*G01F 1/34* (2006.01)

(52) U.S. Cl.
CPC ........... *G01N 23/087* (2013.01); *G01N 33/28* (2013.01); *G01N 33/2823* (2013.01); *G01N 2223/605* (2013.01); *G01N 2223/635* (2013.01); *G01N 2223/637* (2013.01)

(56) References Cited

U.S. PATENT DOCUMENTS

| | | | | |
|---|---|---|---|---|
| 5,822,390 | A * | 10/1998 | Hewitt | G01N 23/12 378/51 |
| 5,854,820 | A * | 12/1998 | Slijkerman | G01N 23/12 378/53 |
| 5,893,642 | A * | 4/1999 | Hewitt | B01F 5/061 366/142 |
| 6,097,786 | A * | 8/2000 | Groves | G01N 23/12 378/52 |
| 6,265,713 | B1 * | 7/2001 | Berard | G01F 1/363 250/269.1 |
| 6,275,563 | B1 * | 8/2001 | Griffin, Jr. | G01N 23/06 378/58 |
| 6,332,351 | B1 * | 12/2001 | Torkildsen | G01N 23/12 250/253 |
| 6,389,908 | B1 * | 5/2002 | Chevalier | G01N 33/2823 73/861.63 |
| 6,405,604 | B1 * | 6/2002 | Berard | G01F 1/74 73/861.04 |
| 7,099,433 | B2 * | 8/2006 | Sommer | G01N 23/06 209/589 |
| 7,105,805 | B2 * | 9/2006 | Berard | G01N 33/2823 250/256 |
| 7,136,451 | B2 * | 11/2006 | Naidu | H05G 1/10 378/112 |
| 7,298,826 | B2 * | 11/2007 | Inazuru | G01N 23/04 378/108 |
| 7,316,166 | B2 * | 1/2008 | Atkinson | G01N 23/12 73/861.63 |
| 7,542,543 | B2 * | 6/2009 | Shampine | G01N 9/24 250/256 |
| 7,561,663 | B2 * | 7/2009 | Watanabe | G01N 23/12 378/207 |
| 7,639,781 | B2 * | 12/2009 | Shampine | G01N 23/12 250/258 |
| 7,676,344 | B2 * | 3/2010 | Chevalier | G01F 1/56 250/306 |
| 7,684,540 | B2 | 3/2010 | Groves et al. | |
| 7,903,782 | B2 * | 3/2011 | Groves | G01N 23/12 250/256 |
| 7,908,930 | B2 * | 3/2011 | Xie | G01N 22/00 73/861.04 |
| 8,116,428 | B2 * | 2/2012 | Gudmundson | G01N 23/04 378/53 |
| 8,472,582 | B2 * | 6/2013 | Roux | G06F 19/703 378/51 |
| 8,718,230 | B2 * | 5/2014 | Luo | G01N 23/12 378/51 |
| 8,742,328 | B2 * | 6/2014 | Simon | G01V 5/125 250/254 |
| 9,086,306 | B2 * | 7/2015 | Polikhov | G01F 1/704 |
| 9,291,579 | B2 * | 3/2016 | Hu | G01N 23/046 |
| 2005/0163284 | A1 | 7/2005 | Inazuru | |
| 2006/0072703 | A1 | 4/2006 | Naidu et al. | |
| 2006/0171504 | A1 | 8/2006 | Sommer et al. | |
| 2007/0189452 | A1 * | 8/2007 | Johnson | G01F 1/58 378/53 |
| 2008/0069307 | A1 * | 3/2008 | Shampine | G01N 9/24 378/194 |
| 2008/0137808 | A1 * | 6/2008 | James | G01N 23/125 378/53 |
| 2010/0140496 | A1 * | 6/2010 | Pinguet | G01N 23/12 250/432 R |
| 2013/0034206 | A1 * | 2/2013 | Cadalen | G01N 33/2823 378/51 |
| 2014/0093037 | A1 * | 4/2014 | Polikhov | G01F 1/7086 378/53 |

* cited by examiner

APPARATUS AND METHOD FOR FLUID PHASE FRACTION DETERMINATION USING X-RAYS

TECHNICAL FIELD

The invention relates generally to the field of measurement of fluid properties using x-ray radiation. More particularly, an aspect relates to an apparatus for fluid phase fraction determination using x-rays. Another aspect relates to a method for fluid phase fraction determination using x-rays. Such a fluid phase fraction determination apparatus and method may be used, in particular but not exclusively, in oilfield related applications, for example, to determine fluid phase fraction and infer flow rates of a hydrocarbon effluent flowing out of a geological formation into a well that has been drilled for the purpose of hydrocarbon exploration and production.

BACKGROUND OF THE INVENTION

Fluid phase fractions are determined using a fluid fractional composition measuring apparatus. A known apparatus comprises a radiation source and detector, wherein the radiation source is a chemical isotope radiation source. The chemical isotope radiation source may be deployed for long periods of time in unattended locations that may encounter variable ambient environmental conditions. As a consequence, there exists a security and environmental risks. Thus, there is a need to use non-chemical radiation sources for fluid fractional composition measuring apparatuses.

An x-rays generator is an electrical radiation generator alleviating some of the foregoing drawbacks. However, such an x-rays generator is subject to voltage and beam current fluctuation. As a consequence, the radiation output also fluctuates. This affects the degree of accuracy of the fluid fractional composition measurements. Thus, there is a need to control the x-rays generator, in particular, the input voltage and target current of the x-rays generator.

U.S. Pat. No. 7,684,540 describes an apparatus and method for determining the phase fraction of a fluid collected downhole comprising an x-ray generator, a filter, a sample cell, and a radiation detector. The filter produces a radiation spectrum with a high energy portion and a low energy portion. Filtered radiation is passed through a sample fluid and the resulting attenuated radiation signal is used in calculating the phase fractions of oil, water, and gas in the sample fluid. A second reference radiation detector measures the radiation directly from the x-ray generator and this measurement is used in normalizing the fraction result. The ratio of the high energy signal to low energy signal of the reference detector is used in controlling the input voltage of the x-ray generator thus ensuring a stable spectrum.

Such an apparatus requires two detectors, namely a measurement detector for measuring the attenuated radiation and a reference detector for controlling the x-ray generator and ensuring a stable spectrum. There is a need to reduce the complexity and the cost of the apparatus for fluid phase fraction determination using x-rays. Further, there is also a need to expand the operational range of the apparatus for fluid phase fraction determination using x-rays.

SUMMARY OF THE INVENTION

It is an object of the present invention to propose an apparatus and/or method for fluid phase fraction determination using x-rays that overcomes one or more of the limitations of the existing apparatuses for fluid phase fraction determination using x-rays, in particular reducing complexity and cost of the apparatus and/or method.

According to one aspect, there is provided an apparatus for determining fluid phase fraction of a multiphase fluid mixture, the apparatus comprising:
- a x-ray generator arranged to emit a x-ray radiation spectrum comprising a low energy region and a high energy region, the high energy region including a Bremsstrahlung spectrum;
- a pipe section through which the multiphase fluid mixture flows comprising a measurement section, said measurement section being coupled to said x-ray generator;
- a detector coupled to said measurement section and arranged to detect x-ray radiation that has passed through said multiphase fluid mixture, the detector being coupled to a multichannel analyzer producing a measurement output comprising a low energy and high energy measurement counts;

wherein the measurement output further comprises a low energy and high energy control counts, in a low energy and high energy control windows located on an edge of the Bremsstrahlung spectrum, respectively; and wherein the apparatus further comprises an electrical parameter control arrangement coupled to the x-ray generator and the detector, the electrical parameter control arrangement being arranged to calculate a first ratio of the high energy control count relative to the low energy control count and a second ratio of the high energy measurement count relative to the low energy measurement count, and to adjust the electrical operation of the x-ray generator based on an electrical parameter control function of said ratios that minimize a dependence of the electrical operation of the x-ray generator on the fluid phase fraction of the multiphase fluid mixture flowing in the measurement section.

The electrical parameter control arrangement may be coupled to a high voltage generator of the x-ray generator, the electrical parameter control arrangement being arranged to adjust an acceleration voltage generated by the high voltage generator.

The electrical parameter control arrangement may be coupled to a cathode of the x-ray generator, the electrical parameter control arrangement being arranged to adjust a current in the cathode of the x-ray generator.

The high voltage generator may operate at around 70-100 kV, and a target of the x-ray generator may be made of gold (Au) having around 5 μm thickness such as to generate a Bremsstrahlung spectrum of energy ranging from around 10 to 100 keV.

The x-ray generator may comprise a filter arranged to generate the x-ray radiation spectrum comprising the low energy region and the high energy region, said filter being a K-edge filter made of Barium Fluoride ($BaF_2$) having around 0.12 cm thickness such as to generate the low energy region ranging from around 10 to 50 keV and high energy region ranging from around 50 to 100 keV.

The x-ray generator and the detector may be coupled to the pipe section through windows made of Boron Carbide ($B_4C$) or other materials with low mass attenuation coefficient for low energy X-rays.

The apparatus may further comprise at least one control and data acquisition arrangement for calculating the fluid phase fraction of the multiphase fluid mixture based on the measurement output comprising the low energy and high energy measurement counts.

The measurement section may be selected from the group consisting of: a Venturi, a V-cone, an orifice plate, and a measurement section having a geometry with a variable cross section area.

The multiphase fluid mixture may be a hydrocarbon effluent comprising gas, oil, and water.

According to another aspect, there is provided a method for determining fluid phase fraction of a multiphase fluid mixture, the fluid phase fraction determination method comprising:
flowing the multiphase fluid mixture in a pipe section having a measurement section;
submitting the multiphase fluid mixture in the measurement section to an x-ray beam of an x-ray generator having an x-ray radiation spectrum comprising a low energy region and a high energy region, the high energy region including a Bremsstrahlung spectrum;
detecting the x-ray radiation that has passed through said multiphase fluid mixture and producing a measurement output comprising a low energy and high energy measurement counts;
wherein the measurement output further comprises a low energy and high energy control counts, in a low energy and high energy control windows located on an edge of the Bremsstrahlung spectrum, respectively;
wherein the fluid phase fraction determination method further comprises:
calculating a first ratio of the high energy control count relative to the low energy control count and a second ratio of the high energy measurement count relative to the low energy measurement count, and an electrical parameter control function of said ratios; and
adjusting the electrical operation of the x-ray generator based on the electrical parameter control function of said ratios that minimize a dependence of the electrical operation of the x-ray generator on the fluid phase fraction of the multiphase fluid mixture flowing in the measurement section.

The step of adjusting the electrical operation of the x-ray generator may comprise adjusting an acceleration voltage generated by a high voltage generator of the x-ray generator, or adjusting the electrical operation of the x-ray generator comprises adjusting a current in a cathode of the x-ray generator.

The acceleration voltage may be adjusted to modify the low energy region and high energy region such as to adapt the x-ray radiation spectrum to a compositional variation during time of the multiphase fluid mixture The electrical parameter control function $F_C(V)$ may be given by:

$$F_{C,x}(V) = \{C_1 \cdot R_{V,x}(V) + C_2 \cdot R_{E,x}(V) + C_3 \cdot (R_{V,x}(V))^2 + C_4 \cdot R_{V,x}(V) \cdot R_{E,x}(V)\}$$

where:
V is the x-ray generator accelerating voltage;
x refers to a particular constituting element in the multiphase fluid mixture;
$R_V$ is the first ratio of the high energy control count relative to the low energy control count;
$R_E$ is the second ratio of the high energy measurement count relative to the low energy measurement count;
and where the coefficients C1, C2, C3 and C4 minimize:

$$\|F_{C,x}(V) - R_{V,x=H2O}(V)\| \text{ or } \|F_{C,x}(V) - R_{V,x=H2O}(V)\|^2.$$

The method may further comprise calculating the fluid phase fraction of the multiphase fluid mixture based on the measurement output comprising the low energy and high energy measurement counts.

According to another aspect, there is provided a flow rate measuring method, wherein the method comprises determining the fluid phase fraction according to the invention, measuring a differential pressure of the multiphase fluid mixture in the measurement section and estimating a total flow rate of the multiphase fluid mixture based on the calculated fluid phase fraction and measured differential pressure.

The apparatus and method enable improving the measurements accuracy by controlling the x-ray generator operating electrical parameter, e.g. in particular the accelerating voltage while avoiding using a reference detector.

The apparatus and method enable expanding the operational range of the apparatus for fluid phase fraction determination using x-rays. In particular, the operational range may now encompass various hydrocarbon effluent compositions from, e.g., heavy oil and high water cut to high gas fraction.

The apparatus and method can be easily adapted to the compositional variation during time of the multiphase fluid mixture produced by the hydrocarbon reservoir by merely changing the x-rays generator voltage. Effectively, it is possible to vary the operating energy as it is driven by the applied voltage.

Further, using an x-ray generator is safer in operation, transportation, and storage compared to traditional chemical radioactive sources.

Other advantages will become apparent from the hereinafter description.

BRIEF DESCRIPTION OF THE DRAWINGS

The present invention is illustrated by way of examples and not limited to the accompanying drawings, in which like references indicate similar elements.

DETAILED DESCRIPTION OF THE INVENTION

In the following description, the terminology "multiphase fluid mixture" has a broad meaning. In the oilfield related applications, it includes a broad range of hydrocarbon effluent compositions. It may be a mixture comprising multiple phases, for example oil, gas and water. The composition of the mixture may vary from heavy oil and high water cut to high gas fraction. It may also be a mixture comprising a single phase in specific conditions, resulting in a separation between the components constituting said phase, for example in conditions above the bubble point, or in non-isobaric or/and non-isothermal conditions. In such conditions, the single phase becomes biphasic and drops heavy components. Moreover, it may also be a 4-phases mixture, the fourth phase being considered to be either the water salinity or sulfur mass fraction (in oil, gas, and water), or injected/produced water ratio (if water is injected into the hydrocarbon reservoir for pressure maintenance purposes), or injected/produced gas ratio (if gas is injected into the hydrocarbon reservoir), etc. . . .

Figure 1:
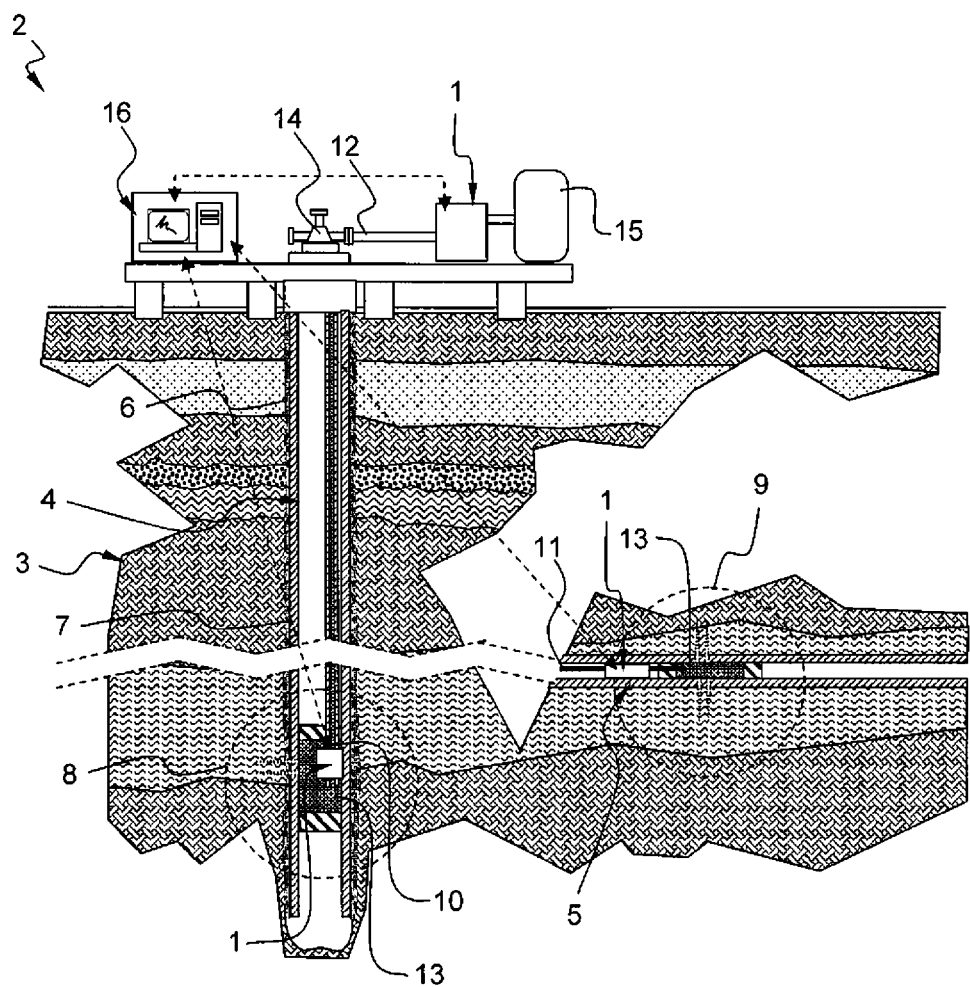
FIG. 1 schematically shows an onshore hydrocarbon well location illustrating various application examples of an apparatus for fluid phase fraction determination using x-rays of the invention.

FIG. 1 schematically shows an onshore hydrocarbon well location and equipments 2 above a hydrocarbon geological formation 3 after drilling operation has been carried out, after a drill pipe has been run, and eventually, after cementing, completion and perforation operations have been carried out, and exploitation has begun. The well is beginning producing hydrocarbon, e.g. oil and/or gas. At this stage, the well bore comprises substantially vertical portion 4 and may also comprise horizontal or deviated portion 5. The well bore is either an uncased borehole, or a cased borehole, or a mix of uncased and cased portions.

The cased borehole portion comprises an annulus 6 and a casing 7. The annulus 6 may be filled with cement or an open-hole completion material, for example gravel pack. Downhole, a first producing section 8 and second producing section 9 of the well typically comprises perforations, production packers and production tubings 10, 11 at a depth corresponding to a reservoir, namely hydrocarbon-bearing zones of the hydrocarbon geological formation 3. A fluid mixture 13 flows out of a first producing section 8 and a second producing section 9 of the hydrocarbon geological formation 3. The fluid mixture 13 is a multiphase hydrocarbon fluid mixture comprising a plurality of fluid fractions (water, oil, gas) and a plurality of constituting elements (water, various hydrocarbon molecules, various molecules solved in water). The fluid mixture 13 flows downhole through the production tubings 10, 11 and out of the well from a well head 14. The well head 14 is coupled to surface production arrangement 15 by a surface flow line 12. The surface production arrangement 15 may typically comprise a chain of elements connected together, e.g. a pressure reducer, a heat exchanger, a pumping arrangement, a separator, a tank, a burner, etc. . . . (not shown in details). In one embodiment, one or more apparatus 1 for fluid phase fraction determination using x-rays may be installed within the surface flow line 12 or connected to the surface flow line 12 or connected downhole to the production tubings 10, 11.

A control and data acquisition arrangement 16 is coupled to the apparatus 1 for fluid phase fraction determination using x-rays, and/or to other downhole sensors (not shown) and/or to active completion devices like valves (not shown). The control and data acquisition arrangement 16 may be positioned at the surface. The control and data acquisition arrangement 16 may comprise a computer. It may also comprise a satellite link (not shown) to transmit data to a client's office. It may be managed by an operator. The control and data acquisition arrangement 16 may determine the total flowrate, the flow rates of the individual phases of the multiphase fluid mixture, the density of the multiphase fluid mixture, the temperature and other values based on the measurements provided by the various sensors and detectors as explained in details hereinafter.

The precise design of the down-hole producing arrangement and surface production/control arrangement is not germane to the present invention, and thus these arrangements are not described in detail herein.

Figure 2:
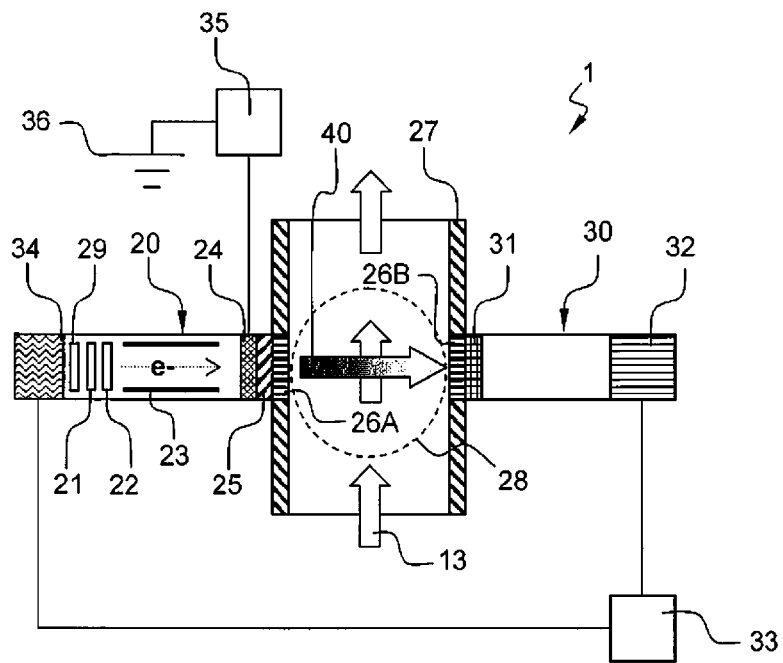
FIG. 2 is a cross-section view schematically illustrating an embodiment of the apparatus for fluid phase fraction determination using x-rays of the invention.

FIG. 2 schematically illustrates an embodiment of the apparatus for fluid phase fraction determination using x-rays of the invention. The apparatus 1 for fluid phase fraction determination comprises an x-ray generator 20, a pipe section 27, a detector 30 coupled to a multichannel pulse height analyzer 32, and an electrical parameter control arrangement 33 coupled to the x-ray generator 20 and the detector 30.

The x-ray generator 20 is arranged to emit an x-ray beam path 40 having a defined radiation spectrum as explained in details hereinafter. As it is known in the art, the x-ray generator 20 may be a grounded target x-ray tube. Nevertheless, any other kind of x-ray tube may be used provided that the acceleration voltage and/or beam current can be controlled. A high voltage generator 34 applies a high voltage to a cathode 21. A small current is used to heat the cathode 21, for example by means of a resistor 29, and causes it to release electrons e–. A grid 22 is arranged to direct electrons released from cathode 21 toward an electron accelerating section 23. The electron accelerating section 23 accelerates the electrons e– toward a target 24. The collision of the electron e– with the target 24 generates a continuous x-ray radiation spectrum, more precisely a Bremsstrahlung spectrum. As an example, the grid 22 is made of Nickel (Ni), and the target 24 is a 5 μm thick foil made of gold (Au).

The pipe section 27 comprises a measurement section 28 where the properties of the multiphase fluid mixture 13 are measured. The measurement section 28 is coupled to the x-ray generator 20 by means of an appropriate entrance window 26A. The x-ray generator 20 and the detector 30 are diametrically positioned on each opposite sides of the measurement section 28 so as to substantially face each other.

The detector 30 is also coupled to the measurement section 28 by means of an appropriate exit window 26B. The detector 30 is a radiation detector arranged to detect the x-ray radiations that have passed through the multiphase fluid mixture 13. The detector 30 can be any type of radiation detector capable of monitoring x-ray radiations. The radiation detector may be a scintillation counter including a scintillation crystal (e.g. doped Sodium Iodide NaI(Tl)) coupled to a photomultiplier. As it is known in the art, radiation entering the crystal will cause the crystal to produce flashes of light, the amplitude of which is proportional to the energy of the entering radiation. Advantageously, the output of the photomultiplier of the detector 30 may be further coupled to a multichannel pulse height analyzer or MCA 32. The MCA 32 may be integrated to the detector 30. The multichannel pulse height analyzer 32 may generate a digital bit or count, or similar signal corresponding to the electrical pulse from the photomultiplier having a selected amplitude, or having amplitude within a selected amplitude range. Typically, an output of the MCA multichannel pulse height analyzer 32 includes numbers of counts for each of a selected number of energy windows or ranges detected by the detector 30 within a determined time interval.

The entrance window 26A and the exit window 26B are similar windows. They are sealed against the pipe section 27 and are transparent to the x-ray in the energy spectrum used by the x-ray generator 20 and the detector 30. Advantageously, each window is made of boron carbide ($B_4C$) and has, as an example, a thickness ranging from a few dozen of millimeters to a few centimeters. The housing of the x-ray generator 20 and detector 30 may be made of Beryllium (Be).

Figure 3:
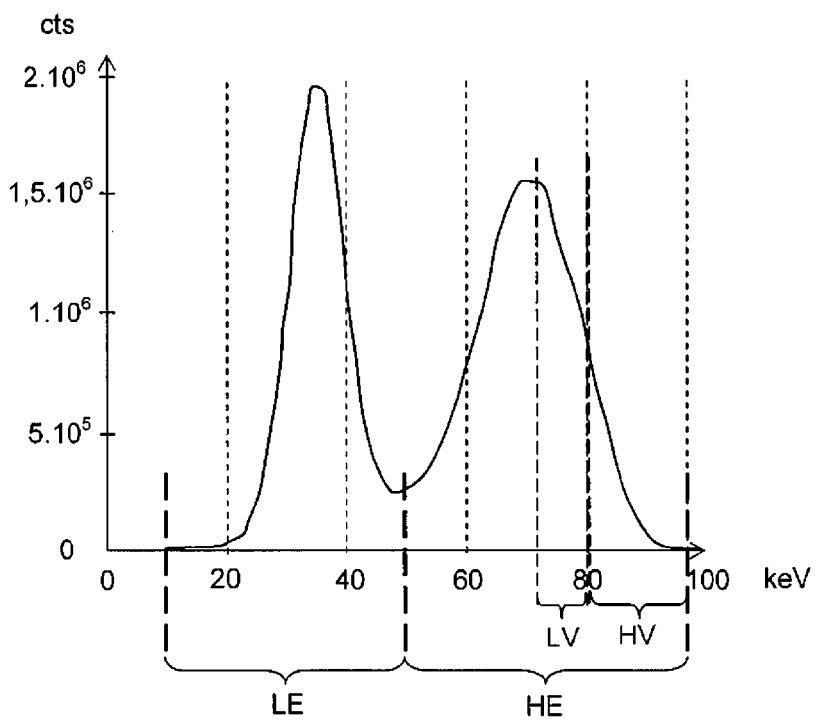
FIG. 3 graphically represents a filtered radiation spectrum measured by the detector and used in the determination of fluid phase fraction according to the invention.

The x-ray generator 20 further comprises a filter 25 that is used to obtain the radiation spectrum as depicted in FIG. 3. The radiation spectrum comprises two distinct energy peaks (local maxima of numbers of photons at each of two distinct energy levels), namely a low energy peak and a high energy peak that are used for the determination of the fluid phase fraction. In particular, in oilfield applications, the low energy peak enables enhancing sensitivity of the measurements to discriminate between oil and water. In one embodiment, the filter 25 is a K-edge filter used to convert the Bremsstrahlung spectrum produced in the x-ray generator 20 into the dual peak spectrum. Advantageously, the K-edge filter is a 0.12 cm thick Barium Fluoride ($BaF_2$) disk. However, any element can be used to filter the radiation as long as a high energy and low energy portion is provided. This K-edge filter is advantageous because it is also transparent to low energy x-ray radiation (i.e. 15-20 keV).

A detector entrance window 31 may be further interposed between the exit window 26B and the detector 30. The detector entrance window 31 may be made of Nickel (Ni).

FIG. 3 graphically represents the filtered radiation spectrum measured by the detector 30 and used in the determination of fluid phase fraction according to the invention. The x-axis represents the energy in keV while y-axis represents the number of counts per keV. The depicted trace is obtained, as an example, with an x-ray generator 20 operating at 85 kV with 10 ρA of electron beam current incident on a 5 μm thick Au target. The resulting Bremsstrahlung x-ray spectrum that exits the x-ray generator 20 passes through a 0.12 cm thick BaF2 K-edge filter before entering the measurement section. In such an example, a low LE energy measurement window ranging 10-50 keV, a high HE energy measurement window ranging 50-100 keV, a low LV energy control window ranging 75-80 keV, and a high HV energy control window ranging 81-100 keV can be defined.

According to the present invention, the low LV and high HV energy control windows are used to control at least one electrical parameter, for example the operating voltage of the x-ray generator 20 as explained in details hereinafter. The electrical parameter control arrangement 33 is coupled to the multichannel pulse height analyzer or MCA 32 of the detector 30 and to the high voltage generator 34 of the x-ray generator 20. In particular, based on the measurements in the low LV and high HV energy control windows, the electrical parameter control arrangement 33 controls the operation of the high voltage generator 34. The electrical parameter control arrangement 33 may regulate the acceleration voltage in the x-ray generator 20 or the current in the cathode 21.

FIGS. 4 to 8 are various graphic representations related to the voltage sensitivity, the voltage being related to the voltage used in the x-ray generator for generating the radiation spectrum. In these Figures, the x-axis represents the fractional change in Volts (i.e. the voltage of the x-ray generator), while the y-axis represents the fractional change in count rate.

Figure 4:
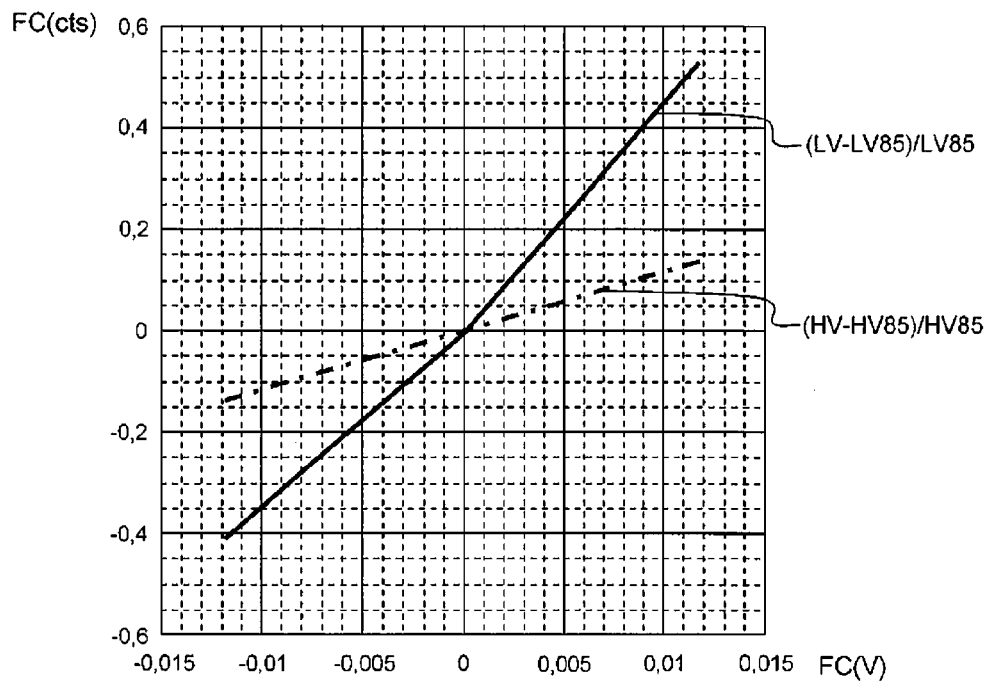
FIG. 4 is a graphic representation of the voltage sensitivities of the high HV and low LV energy control windows of the invention.

FIG. 4 is a graphic representation of the voltage sensitivities of the high HV and low LV energy control windows. The full line represents the voltage sensitivity of the low LV energy control window. The dash-dotted line represents the voltage sensitivity of the high HV energy control window.

Figure 5:
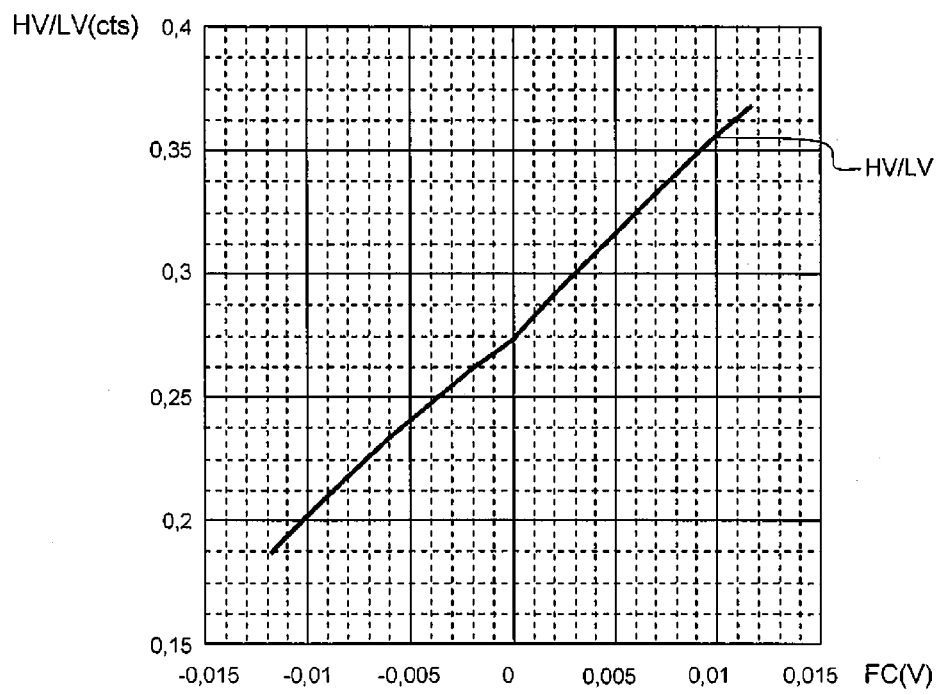
FIG. 5 is a graphic representation of the ratio of high HV energy control window count rate to low LV energy control window count rate as a function of the fractional change of the x-ray generator voltage.

FIG. 5 is a graphic representation of the ratio of high HV energy control window count rate to low LV energy control window count rate as a function of the fractional change of the x-ray generator voltage relative to 85 kV.

Figure 6:
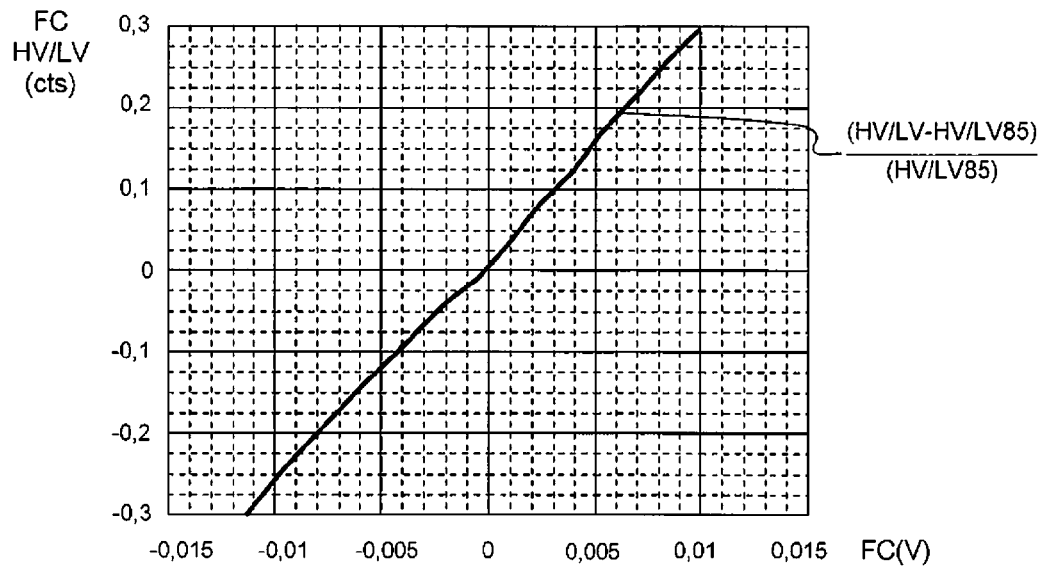
FIG. 6 is a graphic representation of the fractional change in the ratio of high HV energy control window count rate to low LV energy control window count rate as a function of the fractional change of the x-ray generator voltage.

FIG. 6 is a graphic representation of the fractional change in the ratio of high HV energy control window count rate to low LV energy control window count rate as a function of the fractional change of the x-ray generator voltage relative to 85 kV. This graphic representation illustrates that a 1% change in the x-ray generator voltage results in a 30% change in the count rate ratio HV/LV.

Figure 7:
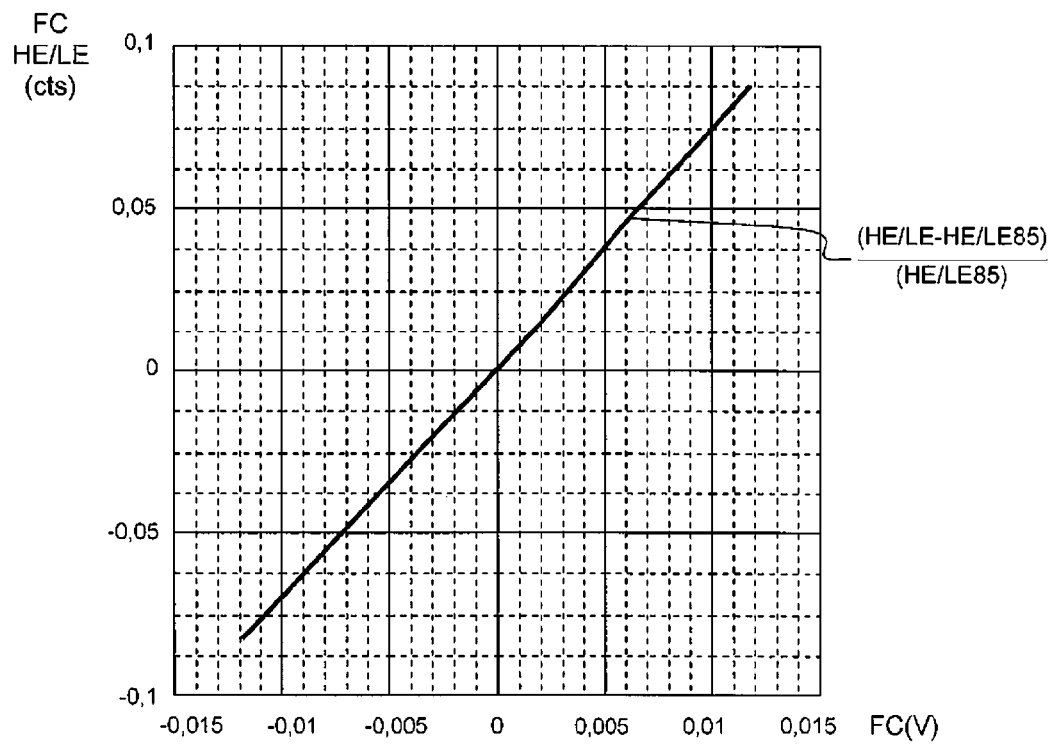
FIG. 7 is a graphic representation of the fractional change in the ratio of high HE energy measurement window count rate to low LE energy measurement window count rate as a function of the fractional change of the x-ray generator voltage.

FIG. 7 is a graphic representation of the fractional change in the ratio of high HE energy measurement window count rate to low LE energy measurement window count rate as a function of the fractional change of the x-ray generator voltage relative to 85 kV. This graphic representation illustrates that a 1% change in the x-ray generator voltage results in about a 7.5% change in the count rate ratio HE/LE.

It is to be noted that the count rates in the low LV and high HV energy control windows are significantly less than in the low LE and high HE energy measurement windows. Nevertheless, the ratio HV/LV based on the count rates in the energy control windows is about four times more sensitive, with respect to the x-ray generator operating voltage, than the ratio HE/LE based on the count rates in the energy measurement windows. Thus, the increased sensitivity of the ratio HV/LV to the x-ray generator voltage compensates the lower count rates in the low LV and high HV energy control windows. Measuring the ratio HV/LV to 0.1% will hold the x-ray generator voltage to 0.003% and the ratio HE/LE to 0.015%. A 0.1% accuracy measurement of the ratio HV/LV is possible since any drift or change in the operation of the x-ray generator 20 is expected to be very slow. In such a situation, according to the present invention, monitoring the ratio HV/LV enables controlling the x-ray generator operating voltage while avoiding using a reference detector as in the prior art, for example as described in U.S. Pat. No. 7,684,540.

As an example, for oilfield applications, targeted specifications for water liquid ratio WLR determination are achieved when a voltage stability of the order of 0.01% is maintained. Taking into account the above voltage sensitivity results, a control ratio HV/LV around 0.3% is required to achieve a voltage stability of around 0.01%. In this situation, assuming that the fluctuations in the measurement ratio HE/LE can be held around 0.015%, the variation of the measurement ratio HE/LE due to changing fluid material flowing through the measurement section of the pipe section 27 is significantly larger than the variation of the measurement ratio HE/LE due to the variation of the x-ray generator voltage. Therefore, it is proposed a voltage control function $F_C(V)$ that maintains the voltage sensitivity of the control ratio HV/LV. As explained hereinbefore, this voltage control function $F_C(V)$ is less sensitive to changes in the composition of the fluid flowing through the measurement section 28 of the pipe section 27. According to an embodiment, the voltage control function $F_C(V)$ is defined as a function of the control ratio RV=HV/LV and measurement ratio RE=HE/LE such that the dependence of the electrical operation of the x-ray generator 20 on the multiphase fluid mixture x (i.e. the constituting elements or composition of the multiphase fluid mixture 13) flowing through the measurement section 28 is minimized, namely:

$$F_{C,x}(V)=\{C_1 \cdot R_{V,x}(V) + C_2 \cdot R_{E,x}(V) + C_3 \cdot (R_{V,x}(V))^2 + C_4 \cdot R_{V,x}(V) \cdot R_{E,x}(V)\} \quad (1)$$

where the subscript x refers to a particular constituting element in the x-ray beam path 40 through the measurement section 28.

The coefficients C1, C2, C3 and C4 are found such that:

$$\|F_{C,x}(V) - R_{V,x=H2O}(V)\| \text{ or}$$
$$\text{alternatively } \|F_{C,x}(V) - R_{V,x=H2O}(V)\|^2 \quad (2)$$

is minimized over all the constituting elements of the fluid likely to be found in the measurement section 28 (for example at a voltage V around 85 kV).

A particular example related to an oilfield application will be presented hereinafter. A set of twelve different constituting elements that might be present in a multiphase fluid mixture 13 flowing out of an hydrocarbon reservoir through the measurement section 28 have been used to derive the coefficient C1, C2, C3 and C4 of the voltage control function $F_C(V)$ (the min square method has been applied), namely:

$$C1 = 1.89$$

$$C2 = -5.64 \times 10^{-3}$$

$$C3 = -3.19$$

$$C4 = 1.94 \times 10^{-2}$$

The following table lists the control ratio HV/LV and the voltage control function $F_C(V)$ values at an accelerating voltage of 85 kV for some sample fluid materials that might be flowing through the measurement section 28. It is to be noted that the sensitivity of the voltage control function $F_C(V)$ relatively to fluid material changes in the measurement section 28 is about ten times smaller than the control ratio. The voltage control function $F_C(V)$ varies by less than 0.1% over the full range of constituting elements likely to be encountered in the measurement section 28. Consequently, as an example, small changes in the water liquid ratio WLR should not cause significant changes in the operating voltage of the x-ray generator 20.

| Material k | HV/LV | $F_{C,x}$ (85 kV) |
|---|---|---|
| $CH_2$ | 0.27781 | 0.27910 |
| $CH_3$ | 0.27798 | 0.27941 |
| $CH_4$ | 0.28105 | 0.27920 |
| $H_2O$ | 0.27918 | 0.27922 |
| $H_2O$ + 250 kppm NaCl | 0.28386 | 0.27919 |

Figure 8:
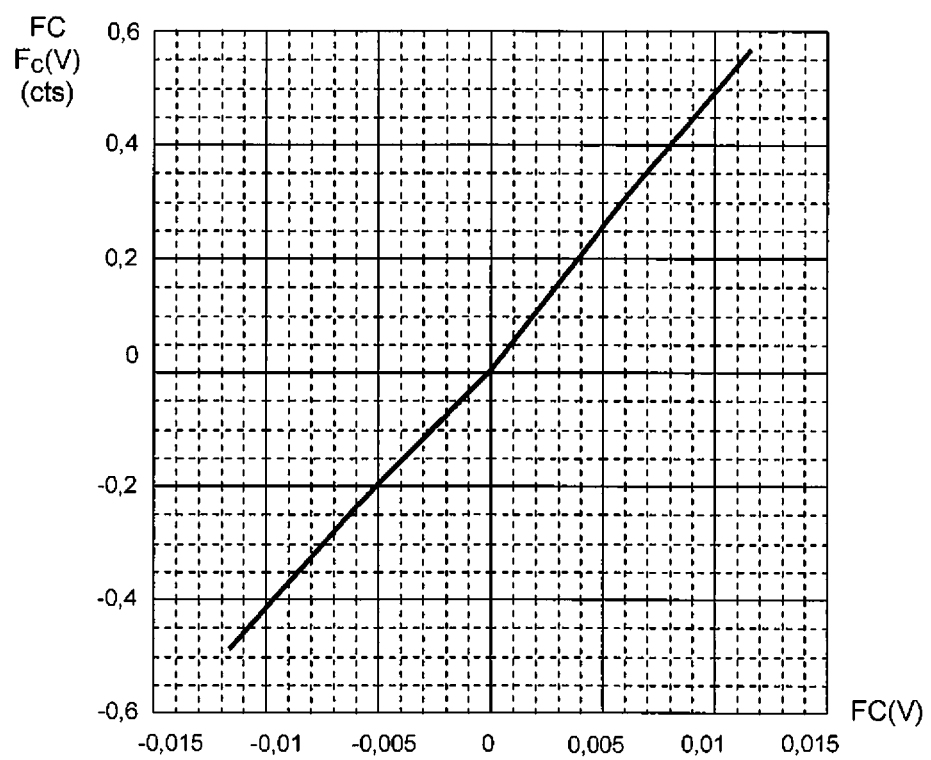
FIG. 8 is a graphic representation of the fractional change in the voltage control function $F_C(V)$ as a function of the fractional change of the x-ray generator voltage.

FIG. 8 is a graphic representation of the fractional change in the voltage control function $F_C(V)$ as a function of the fractional change of the x-ray generator voltage relative to 85 kV. This graphic representation illustrates the voltage dependency of the voltage control function $F_C(V)$. It is to be emphasized that the voltage control function $F_C(V)$ is even more sensitive to the changes in the operating voltage that the ratio HV/LV based on the count rates in the energy control windows plotted in FIG. 6.

According to the present invention, the x-ray generator voltage is controlled and regulated by means of the voltage control function $F_C(V)$ which depends on count rate measurements in four energy windows. In a preferred embodiment of the invention, the voltage control function $F_C(V)$ is implemented by the electrical parameter control arrangement 33. In particular, the electrical parameter control arrangement 33 controls the operation of the high voltage generator 34 that regulates the acceleration voltage in the x-ray generator 20 such as to minimize the dependence on the fluid material flowing through the measurement section 28 of the voltage control function $F_C(V)$ as hereinbefore explained. Two energy measurement windows are the low LE and high HE measurement windows used to determine fractions as described in U.S. Pat. No. 7,684,540 by ways of phase fraction inversions (see FIG. 3). The low LE and high HE measurement windows are positioned such that the boundaries are in regions relatively insensitive to small changes in voltage dividers defining the energy measurement windows LE and HE. The two additional energy windows are the low LV and high HV energy control windows (see FIG. 3). They are located on the edge of the Bremsstrahlung spectrum such that the boundaries are in regions relatively sensitive to small errors in voltage dividers defining the energy control windows LV and HV.

In an embodiment wherein the x-ray generator 20 is a grounded target x-ray tube, the boundaries for the low LV and high HV energy control windows are defined by means of the resistor 29 through which a small current is passed to heat the cathode 21. In particular, the resistor 29 may be carefully selected, mounted and temperature regulated in order to define said boundaries. Further, the measurement of the x-ray generator target current is accomplished by isolating the target 24 from the ground 36 and measuring the current to ground with a sensitive and temperature controlled micro-ammeter 35.

Figure 9:
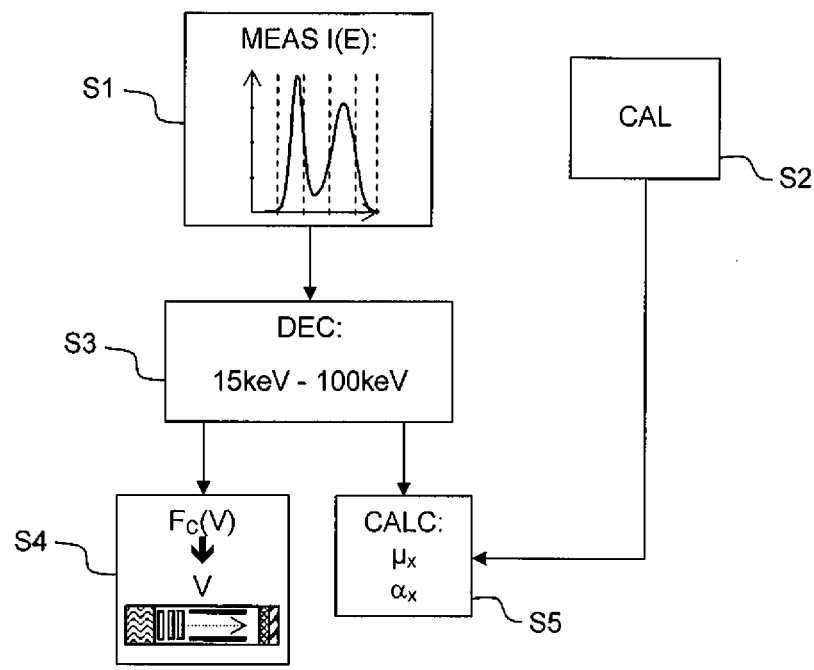
FIG. 9 schematically illustrates the method for fluid phase fraction determination using x-rays of the invention.

FIG. 9 schematically illustrates the method for fluid phase fraction determination using x-rays.

The fluid phase fraction determination requires measuring (step S1) the attenuation I(E) of the x-rays beam 40 of a given energy E and intensity $I_0(E)$, passing through a thickness d of a substance x having a density ρ. The attenuation I(E) can be written as:

$$I(E) = I_0(E) e^{-\mu x(E) \rho d} \quad (3)$$

where:
  μx(E) in m²/kg is the mass attenuation coefficient of the substance x;
  $I_0(E)$ in count per second is the x-ray intensity measured by the detector 30 at the given energy E when the measurement section 28 is empty;
  I(E) in count per second is the x-ray intensity measured by the detector 30 at the given energy E when the substance is in the measurement section 28;
  ρ in kg/m³ is the mass density of the substance; and
  d in meter is the measurement section thickness.

A calibration or a series of calculations (step S2) may be performed based on the known chemistry (e.g. type of oil, gas and water) of the multiphase fluid mixture 13 that is flowing in the measurement section 28 of the apparatus 1.

According to an embodiment the present invention, the determination of multiphase fluid mixture properties is based on the spectra deconvolution (step S3), namely the processing of the x-ray spectra in the whole range of x-ray energy (e.g. from 15 keV to 100 keV). This is possible because, on the one hand, the x-ray generator 20 together with the filter 25 allows submitting the multiphase fluid mixture 13 to said x-ray spectra in the whole range of x-ray energy, and, on the other hand, the detector 30 together with the MCA multichannel pulse height analyzer 32 allows proceeding with multichannel detection of x-ray radiation digitizing spectra with only a few keV steps. The entire spectra is detected and recorded. Firstly, the dip between the two peaks LE and HE is used to control (step S4) x-ray generator voltage by means of the voltage control function $F_C(V)$ as hereinbefore explained. An insignificant change in the x-ray generator voltage leads to the significant change in the x-ray emission. In particular, according to the present invention, the low energy and high energy can be changed by varying high voltage.

The knowledge of the low energy part of the spectra (e.g. 15-20 keV) together with the low and high energy peaks enables calculating (step S5) more than two variables (which are usually measured by a multiphase meter, for example gas fraction and water cut). The mass attenuation coefficient for i-energy level for constituting element x can be written as:

$$\mu_x^i(Z, A, \rho) = a_1^i \frac{Z_x}{A_x} \rho_x + a_2^i \frac{Z_x^C}{A_x} \rho_x \quad (4)$$

where the first term is related to the Compton scattering and the second term is related to the photoelectric effect (C is usually around 4 to 5). The same can be written for the substance instead of chemical element, but using effective Z-number and effective value of photoelectric factor. The algorithm used for the volume fraction determination of the different phases is based on the solution of a set of linear equations of the phases attenuation properties, and also the sum of volume fraction, namely:

$$\begin{pmatrix} \mu_o^{low} & \mu_w^{low} & \mu_g^{low} & \mu_4^{low} \\ \mu_o^{LE} & \mu_w^{LE} & \mu_g^{LE} & \mu_4^{LE} \\ \mu_o^{HE} & \mu_w^{HE} & \mu_g^{HE} & \mu_4^{HE} \\ 1 & 1 & 1 & 1 \end{pmatrix} \begin{pmatrix} \alpha_o \\ \alpha_w \\ \alpha_g \\ \alpha' \end{pmatrix} = \begin{pmatrix} \mu^{low} \\ \mu^{LE} \\ \mu^{HE} \\ 1 \end{pmatrix} \quad (5)$$

where:
$\alpha_o$ is the fluid phase fraction of oil, $\alpha_w$ is the fluid phase fraction of water, and $\alpha_g$ is the fluid phase fraction of gas—these fractions are unknown and are the subject of interest;
$\mu_o^{low}, \mu_o^{LE}$ and $\mu_o^{HE}$; $\mu_w^{low}, \mu_w^{LE}$ and $\mu_w^{HE}$; $\mu_g^{low}, \mu_g^{LE}$ and $\mu_g^{HE}$; $\mu_{low}, \mu^{LE}$ and $\mu^{HE}$ are the mass attenuation coefficient of oil, water, gas and multiphase fluid mixture 13 for the low energy part of the spectra, low energy LE and high energy HE measurement windows, respectively; and
$\mu_4^{low}, \mu_4^{LE}$ and $\mu_4^{HE}$ are the mass attenuation coefficient, and $\alpha'$ is the fraction of a fourth substance, for example sulfur, chlorine or salt content.

The low LE energy could mean any energy between e.g. 15 to 50 keV. The high HE energy could mean any energy between e.g. 50 to 100 keV. The low energy part of the spectra could mean any energy between e.g. 15 to 20 keV.

The mass attenuation coefficient combined with the set of linear equations gives:

$$a_1^i \left( \alpha_o \frac{Z_o}{A_o} \rho_o + \alpha_w \frac{Z_w}{A_w} \rho_w + \alpha_o \frac{Z_g}{A_g} \rho_g + \alpha_o \frac{Z'}{A'} \rho' \right) + \quad (6)$$

$$a_2^i \left( \alpha_o \frac{Z_o^C}{A_o} \rho_o + \alpha_w \frac{Z_w^C}{A_w} \rho_w + \alpha_o \frac{Z_w^C}{A_g} \rho_g + \alpha_o \frac{Z'^C}{A'} \rho' \right) =$$

$$\mu^i, i = \text{low}, LE, HE$$

and $$\alpha_o + \alpha_g + \alpha_w + \alpha' = 1 \quad (7)$$

These equations are not independent and it is not possible to estimate more than three unknowns if only Compton and photoelectric effects take place. This is not the case as the photoelectric effect contribution cannot be expressed by the unique representation $$\frac{Z_x^C}{A_x},$$

it may deviate from constituting element to constituting element on a few percents depending on the substance K-edge level and the x-ray energy. However, if there are x-rays with energy below around 20 keV, than Raleigh scattering is also playing a role and the attenuation coefficient can be written as (including the elements of interest: chlorine and sulfur):

$$\mu_x^i(Z, A, \rho) = a_1^i \frac{Z_x}{A_x} \rho_x + a_2^i \frac{Z_x^C}{A_x} \rho_x + a_3^i \frac{Z_x^2}{A_x} \rho_x \quad (8)$$

Thus, in this case, information about the fourth phase could be determined.

Further, the analysis of the complete spectra may be used to estimate the water cut, the gas volume fraction, the sulfur content in the multiphase fluid mixture 13, and/or the water salinity, etc. . . . . .

The apparatus and method enable determining fluid phase fractions in a wide range of fluid properties, namely from very low attenuation like in high gas fraction up to very high attenuation as in the heavy oil and low gas fraction.

The invention enables measurements in a more stable condition because a change in the ratio immediately generates an adjustment of the voltage of the x-ray generator 20 resulting in a more stable output of the x-ray generator 20.

Figure 10:
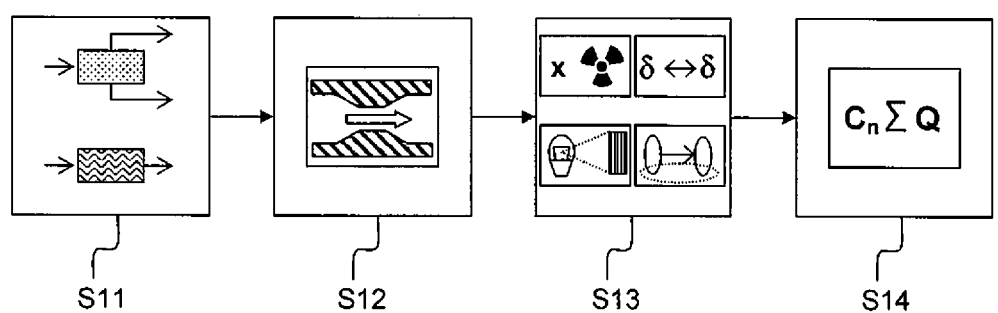
FIG. 10 schematically illustrates the principle of determining the flow rates of the multiphase flow mixture.

FIG. 10 schematically illustrates the principle of determining the flow rate of the multiphase fluid mixture 13. This principle is well known in the art, for example such a principle is described in WO 99/10712 where a traditional chemical radioactive source is used. The stream of the multiphase flow mixture 13 is pre-conditioned (step S11). The multiphase flow mixture 13 is passed through the measurement section 28 of the pipe section 27 and differential pressure is measured (step S12). Though, the measurement section 28 may be a Venturi flow meter, what is important is the generation of a pressure drop when the multiphase fluid mixture 13 flows through the pipe section 27. This could also be obtained with a V-cone, or orifice plate type flow meter. Other measurements are performed (step S13) to determine parameters characterizing each individual phases (liquid hydrocarbon/oil, water, gas). The total flow rate, the flow rates of each individual phase are calculated (step S14) based on said measurements, said parameters and also a fluid model, and taking into consideration some correction factor related to the composition of the multiphase fluid mixture 13 flowing out of the producing sections of the well.

It should be appreciated that embodiments of the present invention are not limited to onshore hydrocarbon wells and can also be used offshore or in subsea applications. Furthermore, although some embodiments have drawings showing a horizontal well bore and a vertical well bore, said embodiments may also apply to a deviated well bore. All the embodiments of the present invention are equally applicable to cased and uncased borehole (open hole). The present invention finds advantageous, though non limitative, applications in the oilfield industry, including various hydrocarbon exploration and production related applications, for example permanent well monitoring applications wherein several measuring apparatuses are positioned at various locations in the field, mobile testing, laboratory testing, artificial lift optimization, surface or subsea locations, etc. . . . Those of ordinary skill in the art will recognize that these are merely examples of possible uses. Although particular applications of the present invention relate to the oilfield industry, other applications to other industry, for example the mining industry or the like also apply.

It may also be apparent for the skilled person that the position and orientation of the x-ray generator 20 and detector 30 relatively to the pipe section 27 as depicted in FIG. 2 is a mere example. This position and orientation can be changed such that said x-ray generator 20 and detector 30 are, for example for the purpose of size saving, positioned in line with, or inclined relatively to the pipe section 27.

Although a drawing shows different functional entities as different blocks, this by no means excludes implementations in which a single entity carries out several functions, or in which several entities carry out a single function. In this respect, the drawings are very diagrammatic.

Thus, the drawings and their description hereinbefore illustrate rather than limit the present invention.

Any reference sign in a claim should not be construed as limiting the claim. The word "comprising" does not exclude the presence of other elements than those listed in a claim. The word "a" or "an" preceding an element does not exclude the presence of a plurality of such element.

The invention claimed is:

1. An apparatus for determining fluid phase fraction of a multiphase fluid mixture, the apparatus comprising:
   an x-ray generator arranged to emit an x-ray radiation spectrum comprising a Bremsstrahlung spectrum including a low energy region and a high energy region;
   a pipe section through which the multiphase fluid mixture flows comprising a measurement section, said measurement section being coupled to said x-ray generator;
   a multichannel analyzer;
   a detector coupled to said measurement section and arranged to detect an x-ray radiation spectrum that has passed through said multiphase fluid mixture, the detector being coupled to the multichannel analyzer producing a measurement output comprising a low energy measurement count (LE) and a high energy measurement count (HE) and a low energy control count (LV) and a high energy control count (HV), the low energy control count (LV) and the high energy control count (HV) determined from a low energy control window and a high energy control window, wherein each control window is located along an edge of the Bremsstrahlung spectrum, respectively; and
   an electrical parameter control arrangement coupled to the x-ray generator and the detector, the electrical parameter control arrangement being arranged to calculate a first ratio ($R_V$) of the high energy control count (HV) relative to the low energy control count (LV) ($R_V$=HV/LV) and a second ratio ($R_E$) of the high energy measurement count (HE) relative to the low energy measurement count (LE) ($R_E$=HE/LE), and to adjust an electrical operation of the x-ray generator based on an electrical parameter control function ($F_C(V)$) of said ratios that minimizes a dependence on the fluid phase fraction of the multiphase fluid mixture flowing in the measurement section.

2. The apparatus according to claim 1, further comprising a high voltage generator, wherein the electrical parameter control arrangement is coupled to the high voltage generator of the x-ray generator, the electrical parameter control arrangement being arranged to adjust an acceleration voltage generated by the high voltage generator.

3. The apparatus according to claim 2, wherein the high voltage generator operates at around 85 kV, and a target of the x-ray generator is made of gold (Au) having around 5 µm thickness such as to generate a Bremsstrahlung spectrum of energy ranging from around 10 to 100 keV.

4. The apparatus according to claim 1, wherein the x-ray generator comprises a cathode, wherein the electrical parameter control arrangement is coupled to the cathode of the x-ray generator, the electrical parameter control arrangement being arranged to adjust a current in the cathode of the x-ray generator.

5. The apparatus according to anyone of the claim 1, wherein the x-ray generator comprises a filter arranged to generate the low energy region and the high energy region of the Bremsstrahlung spectrum, said filter being a K-edge filter made of Barium Fluoride ($BaF_2$) having around 0.12 cm thickness such as to generate the low energy region ranging from around 10 to 50 keV and high energy region ranging from 50 to 100 keV.

6. The apparatus according to claim 1, further comprising windows made of boron carbide ($B_4C$), wherein the x-ray generator and the detector are coupled to the pipe section through the windows.

7. The apparatus according to claim 1, further comprising at least one control and data acquisition arrangement for calculating the fluid phase fraction of the multiphase fluid mixture based on the measurement output comprising the low energy (LE) and high energy (HE) measurement counts.

8. The apparatus according to claim 1, wherein the measurement section is selected from the group consisting of: a Venturi, a V-cone, and an orifice plate.

9. The apparatus according to claim 1, wherein the multiphase fluid mixture is a hydrocarbon effluent comprising gas, oil, and water.

10. A method for determining fluid phase fraction of a multiphase fluid mixture, the method comprising:
    flowing the multiphase fluid mixture in a pipe section having a measurement section;
    submitting the multiphase fluid mixture in the measurement section to an x-ray beam of an x-ray generator having an x-ray radiation spectrum comprising a Bremsstrahlung spectrum including a low energy region and a high energy region;
    detecting the x-ray radiation spectrum that has passed through said multiphase fluid mixture and producing a measurement output comprising a low energy measurement count (LE) and a high energy measurement count (HE) and a low energy control count (LV) and a high energy control count (HV), the low energy control count (LV) and the high energy control count (HV) determined from a low energy control window and a high energy control window, wherein each control window is located along an edge of the Bremsstrahlung spectrum, respectively;
    calculating a first ratio ($R_V$) of the high energy control count (HV) relative to the low energy control count (LV) ($R_V$=HV/LV) and a second ratio ($R_E$) of the high energy measurement count (HE) relative to the low energy measurement count (LE) ($R_E$=HE/LE), and an electrical parameter control function ($F_C(V)$) of said ratios; and adjusting an electrical operation of the x-ray generator based on the electrical parameter control function ($F_C(V)$) of said ratios that minimized a dependence on the fluid phase fraction of the multiphase fluid mixture flowing in the measurement section.

11. The method according to claim 10, wherein adjusting the electrical operation of the x-ray generator comprises adjusting an acceleration voltage generated by a high voltage generator of the x-ray generator.

12. The method according to claim 11, wherein adjusting the acceleration voltage comprises modifying the low energy region and the high energy region to adapt the x-ray radiation spectrum to a compositional variation during time of the multiphase fluid mixture.

13. The method according to claim 10, wherein adjusting the electrical operation of the x-ray generator comprises adjusting a current in a cathode of the x-ray generator.

14. The method according to claim 10, wherein the electrical parameter control function $F_C(V)$ is given by:

$$F_{C,x}(V) = \{C_1 \cdot R_{V,x}(V) + C_2 \cdot R_{E,x}(V) + C_3 \cdot R_{V,x}(V) \cdot R_{E,x}(V)\}$$

where:
V is the x-ray generator accelerating voltage;
x refers to a particular constituting element in the multiphase fluid mixture;
$R_V$ is the first ratio of the high energy control count relative to the low energy control count ($R_V = HV/LV$);
$R_E$ is the second ratio of the high energy measurement count relative to the low energy measurement count ($R_E = HE/LE$);
and where the coefficients C1, C2, C3 minimize:

$$\|F_{C,x}(V) - R_{V,x=H2O}(V)\|.$$

15. The method according to claim 10, further comprising calculating the fluid phase fraction of the multiphase fluid mixture based on the measurement output comprising the low energy measurement count (LE) and the high energy measurement count (HE).

16. A method for determining fluid phase fraction of a multiphase fluid mixture, the method comprising:

flowing the multiphase fluid mixture in a pipe section having a measurement section;

submitting the multiphase fluid mixture in the measurement section to an x-ray beam of an x-ray generator having an x-ray radiation spectrum comprising a Bremsstrahlung spectrum including a low energy region and a high energy region;

detecting the x-ray radiation spectrum that has passed through said multiphase fluid mixture and producing a measurement output comprising a low energy measurement count (LE) and a high energy measurement count (HE) and a low energy control count (LV) and a high energy control count (HV), the low energy control count (LV) and the high energy control count (HV) determined from a low energy control window and a high energy control window, wherein each control window is located along an edge of the Bremsstrahlung spectrum, respectively;

calculating a first ratio ($R_V$) of the high energy control count (HV) relative to the low energy control count (LV) ($R_V = HV/LV$) and a second ratio ($R_E$) of the high energy measurement count (HE) relative to the low energy measurement count (LE) ($R_E = HE/LE$), and an electrical parameter control function ($F_C(V)$) of said ratios;

adjusting an electrical operation of the x-ray generator based on the electrical parameter control function (FC (V)) of said ratios that minimize a dependence on the fluid phase fraction of the multiphase fluid mixture flowing in the measurement section;

calculating the fluid phase fraction of the multiphase fluid mixture based on the measurement output comprising the low energy measurement count (LE) and the high energy measurement count (HE);

measuring a differential pressure of the multiphase fluid mixture in the measurement section; and estimating a total flow rate of the multiphase fluid mixture based on the calculated fluid phase fraction and measured differential pressure.

* * * * *